United States Patent
Xu et al.

(10) Patent No.: US 6,334,775 B2
(45) Date of Patent: *Jan. 1, 2002

(54) CONTINUOUS FIBER-REINFORCED DENTAL RESTORATIONS

(75) Inventors: Huakun Xu, Gaithersburg; Frederick C. Eichmiller, Ijamsville; Gary E. Schumacher, Gaithersburg, all of MD (US)

(73) Assignee: American Dental Association Health Foundation, Chicago, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/250,690

(22) Filed: Feb. 16, 1999

(51) Int. Cl.$^7$ .................................. A61C 5/00
(52) U.S. Cl. ..................... 433/228.1; 433/220; 433/224
(58) Field of Search ............................... 433/228.1, 224, 433/220, 221

(56) References Cited

U.S. PATENT DOCUMENTS

| | | | |
|---|---|---|---|
| 3,962,267 A | 6/1976 | Suzuki et al. | 260/29.6 |
| 4,360,605 A | 11/1982 | Schmitt et al. | 523/116 |
| 4,527,979 A | 7/1985 | McLean et al. | 433/228 |
| 4,738,722 A | 4/1988 | Ibsen et al. | 106/35 |
| 4,894,012 A | 1/1990 | Goldberg et al. | 433/215 |
| 5,098,304 A | 3/1992 | Scharf | 433/215 |
| 5,130,347 A | 7/1992 | Mitra | 522/149 |
| 5,154,762 A | 10/1992 | Mitra et al. | 106/35 |
| 5,189,077 A | 2/1993 | Kerby | 523/116 |
| 5,328,372 A | * 7/1994 | Reynaud et al. | 433/220 |
| 5,367,002 A | 11/1994 | Huang | 423/116 |
| 5,427,613 A | 6/1995 | Arnold | 106/35 |
| 5,445,770 A | 8/1995 | Adams et al. | 264/16 |
| 5,564,929 A | * 10/1996 | Alpert | 433/224 |
| 5,861,445 A | * 1/1999 | Xu et al. | 523/116 |

OTHER PUBLICATIONS

Ladizesky et al. "Acrylic resin reinforced with chopped high performance polyethylene fiber—properities and denture construction" Dent Mater 9:128–135 Mar. 1993.*

A.J. Goldberg & C.J. Burstone "The use of continuous fiber reinforcement in dentistry" Dent Mater 8:197–201, May, 1992.

Malquarti et al. "Prosthetic use of carbon fiber–reinforced epoxy resin for esthetic crowns and fixed partial dentures" The Journal of Prosthetic Dentistry vol. 63, No. 3 Mar. 1990.

(List continued on next page.)

Primary Examiner—John J. Wilson
(74) Attorney, Agent, or Firm—Banner & Witcoff, Ltd.

(57) ABSTRACT

Continuous fibers, resin-fiber pastes, or continuous fiber-reinforced preforms are inserted into tooth cavities to form high-strength dental restorations. The fibers may be mixed or coated with a resin monomer and may be used with fillers such as fluoride-releasing fillers and colorants. The resin-fiber mixture may be hardened into preforms suitable for inserting into tooth cavities. Conventional filling materials such as composite resins and glass ionomers may be used to complete the restoration. Other applications include endodontic posts, retention pins, provisional restorations, and indirect restorations. Fiber reinforcement results in strength, toughness and elastic modulus (stiffness) several times greater than those of currently available direct-filling composite resins. The fiber performs are easily handled and placed into tooth cavities; the restorations are aesthetic and wear compatible, and release fluoride. The final restoration has significantly reduced polymerization shrinkage because the fiber preform can be pre-hardened and therefore will shrink little during hardening of the final restoration.

24 Claims, 3 Drawing Sheets

OTHER PUBLICATIONS

Vallittu et al. "Transverse strength and fatigue of denture acrylic–glass fiber composite" Dent Mater 10:116–121, Mar. 1994.

Goldberg et al. "Screening of matrices and fibers for reinforced thermoplastics intended for dental applications" Journal of Biomedical Materials Research, vol. 28, 167–173 (1994).

Ekstrand et al. "Carbon/raphite fiber reinforced poly(methyl methacrylate): Properties under dry and wet conditions" Journal of Biomedical Materials Research, vol. 21, 1065–1080 (1987).

Bjork & Elkstrand "Implant–fixed, dentla bridges from carbon/graphite fibre reinforced poly (methyl methacrylate)" Carbon fibre PMMA bridges 1986.

Vallittu et al. "Transverse strenght and fatigue of denture acrylic–glass fiber composite" Dent Mater 10:116–121, Mar. 1994.

Altieri et al. "Longitudinal clinical evaluation of fiber–reinforced composite fixed partial dentures: A pilot study" The Journal of Prosthetic Dentistry vol. 71, No. 1, Jan. 1994.

Ruyter et al. "Development of carbon graphite fiber reinforced poly(methyl methacrylate) suitable for implant–fixed dental bridges" Dent Mater 1986: 2: 6–9.

Henry et al. "Fiber–reinforced plastics for interim restorations" Fixed Partial Dentures pp. 110–123 QDT 1990/1991.

Bayne et al. "Update on dental composite restorations" JADA, vol. 125, Jun. 1994, pp. 687–701.

Mazer et al. "Evaluating a Microfill posterior composite resin—A five–year study" JADA, vol. 123, Apr. 1992 pp. 33–38.

Jordan et al. "Posterior Composite Restorations" JADA, vol. 123, Nov. 1991, pp. 31–37.

Jack L. Ferracane et al. "Using posterior composites appropriately" JADA, vol. 123, Jul. 1992, pp. 53–58.

* cited by examiner

CONTINUOUS FIBER-REINFORCED DENTAL RESTORATIONS

FIELD OF THE INVENTION

The present invention relates to dental restorations, and more particularly to reinforced direct and indirect restorations.

BACKGROUND OF THE INVENTION

Direct filling materials are materials that are filled into a tooth cavity and then hardened. Currently available dental direct-filling materials include amalgam, composite resin, glass ionomer cement, and resin-glass ionomer hybrid materials. Indirect filling materials are materials that are hardened or fabricated in a dental laboratory and then fitted either into a tooth cavity or onto a prepared tooth in a dental clinic.

Dental amalgam has been widely used as a direct-filling material for more than a century. The mercury that amalgam contains, however, raises concerns about its toxicity and environmental hazards. As a result, an increasing number of countries have discontinued or are discontinuing the use of amalgam (Hickel, 1996, Acad Dent. Mater. Trans. 9:105–129).

Glass ionomer materials, based on acid-base reactions of polyacid with fluorosilicate glass, possess desirable properties such as fluoride release and adhesion to teeth. However, the inferior mechanical properties, especially their extreme brittleness and low strength, have severely limited their use (Wilson and McLean, 1988, Glass-ionomer Cement, Quintessence Pub). The more recently developed resin-glass ionomer hybrid materials possess improved mechanical properties, but they are still not strong enough for use in posterior restorations with significant occlusal contact (Blackwell and Kase, 1996, Acad. Dent. Mater. Trans. 9:77–88; Hickel, 1996, Acad. Dent. Mater. Trans. 9:105–129).

Composite resins, although one of the most promising aesthetic alternatives to amalgam, have drawbacks such as low durability and fracture, especially in large stress-bearing posterior applications (Corbin and Kohn, 1994, JADA125:381–388; Bayneetal., 1994, JADA125:687–701; Wilder et al., 1996, Acad. Dent. Mater. Trans. 9:151–169). The recently developed composite resins exhibit greatly improved wear characteristics, with low wear rates of the composite and the antagonistic enamel (Suzuki et al., 1996, JADA127:74–80). However, to date, composite resins are used only in relatively small restorations with limited occlusal contact without cusp replacement (Wilder et al., 1996, Acad. Dent. Mater. Trans. 9:151–169). The use of composite resins in larger restorations involving cusp replacement is severely limited by the low toughness of the composites. Indeed, analysis of crack propagation in dental restorations confirmed scanning electron microscope observations that composite resin restorations, although exhibiting low wear rates, are prone to bulk fracture with crack propagation rates higher than those of porcelain (Sakaguchi et al., 1992, Dent. Mater. 8:131–136). Clinical observations coupled with finite element analysis showed that during mastication, the inner side of the restoration can be in maximum tension, leading to fracture initiation (Kelly et al., 1995, J Dent. Res. 74:1253–1258).

Reinforcement with continuous fibers has been shown to impart strength, toughness, and fracture resistance to a matrix material (Goldberg U.S. Pat. No. 4,894,012; Scharf U.S. Pat. No. 5,098,304; Goldberg and Burstone, 1992, Dent. Mater. 8:197–202; Adam U.S. Pat. No. 5,445,770). In dentistry, continuous fibers have been proposed for use in the reinforcement of denture base resins (DeBoer et al., J Prosthet. Dent. 51:119–121; Grave et al., 1985, Dent. Mater. 1:185–187; Yazdanie and Mahood, 1985, J Prosthet. Dent. 54:543–547), splints (Levenson, 1986, JADA112:79–80), retainers (Mullarky, 1985, J Clin. Orthod. 19:655–658; Diamond, 1987, J Clin. Orthod. 21:182–183), fixed prosthodonic appliances (Malquarti et al., 1990, J Prosthet. Dent. 63:251–257; Goldberg et al., 1994, J Biomed. Mater. Res. 28:167–173), and more recently fixed partial dentures (Altieri et al., 1994, J Prosthet. Dent. 71:16–22; Freilich et al., 1997, abstract 999, J Dent. Res. 76:138). The use of continuous fibers in tooth cavity restorations, however, has not been pursued. Continuous fibers have not previously been used to fabricate preforms with shapes and sizes suitable for filling into tooth cavities. Continuous fibers have not previously been used for the reinforcement of dental direct-filling restorations. Continuous fibers have not previously been mixed with fluoride-releasing fillers and fabricated into preforms for use in dental restorations.

SUMMARY OF THE INVENTION

According to the present invention, a method for direct filling a tooth cavity is provided. A fiber material selected from the group consisting of a hardened fiber composite preform, fibers, an unhardened fiber-resin paste, and a partially-hardened flexible fiber composite preform is inserted into a prepared tooth cavity. Fibers in the fiber material extend continuously across at least 60% of the widest dimension of the tooth cavity. After the fiber material has been placed into the tooth cavity, the rest of the tooth cavity is filled with a conventional direct-filling material. The direct-filling material is then hardened.

According to another aspect of the invention, a method for preparing a dental indirect restoration is provided. A fiber material is placed into a mold having a longitudinal axis. The fiber material is selected from the group consisting of a hardened fiber composite preform, fibers, an unhardened fiber-resin paste, and a partially-hardened flexible fiber composite preform. Fibers in the fiber material extend continuously across at least 60% of the widest dimension of the mold. A composite resin filling material is added to the mold. The filling material is hardened to form the dental indirect restoration.

An indirect dental restoration also is provided by the present invention. The restoration comprises fibers which extend continuously across at least 60% of the widest dimension of the restoration, and a filling resin.

According to yet another aspect of the invention, a method is provided for making a composite fiber preform for direct dental restoration. Fibers are selected from the group consisting of glass fibers, ceramic fibers, polymeric fibers, metal fibers, and mixtures thereof. A resin is coated onto the fibers. The resin is hardened to form a composite fiber preform. Fibers extend continuously through at least 60% of the widest dimension of the preform.

According to a further aspect of the invention, a method is provided for making a composite fiber preform for direct dental restoration. Fibers are selected from the group consisting of glass fibers, ceramic fibers, polymeric fibers, metal fibers, and mixtures thereof. A resin is coated onto the fibers. The resin is hardened to form a composite fiber mass. The composite fiber mass is shaped into a composite fiber preform by at least one of cutting and machining. Fibers extend continuously through at least 60% of the widest dimension of the preform.

A composite fiber preform for dental restorations also is provided by the present invention. The preform includes fibers selected from the group consisting of glass fibers, ceramic fibers, polymer fibers, metal fibers, and mixtures thereof, and a resin. Fibers extend continuously through at least 60% of a widest dimension of the preform.

A dental restoration kit also is provided by the present invention. The kit comprises a preform and a composite filling material. Fibers extend continuously through at least 60% of a widest dimension of the preform.

The present invention thus provides dental restorations, tools and methods for making them, which have improved strength, toughness, and stiffness, and reduced polymerization shrinkage. In addition, the restorations are more easily handled and replaced, and have enhanced aesthetics and wear compatibility.

DETAILED DESCRIPTION OF THE INVENTION

Figure 1:
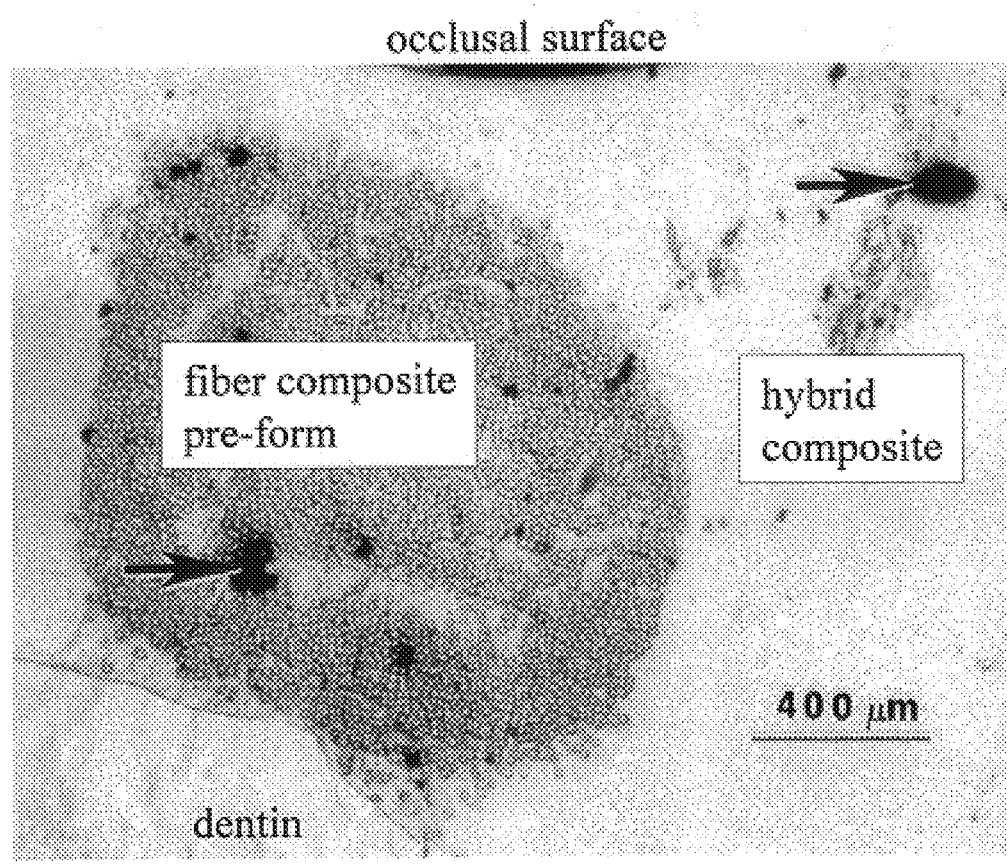
FIG. 1 is an optical micrograph showing a restoration of the present invention, with a fiber preform surrounded by a hybrid posterior composite beneath the occlusal surface.

It is a discovery of the present invention that continuous fibers can be used to fill a tooth cavity by direct filling. A fiber material can be inserted into a prepared tooth cavity, followed by filling the tooth cavity with a direct-filling material. The restoration can then be hardened. The fiber material can be a hardened, continuous fiber composite preform; an unhardened, continuous fiber-resin paste; a partially-hardened, flexible, continuous fiber preform; or continuous fibers per se. The term "continuous fibers" refers to fibers that are either aligned, uniform, or in mesh, rope, thread, or other suitable shapes, which extend continuously through at least 60% of a widest dimension of the tooth cavity (or a dental restoration, preform, or the like). The continuous fibers may extend continuously through 65%, 70%, 75%, or even 80% or more of the widest dimension of the tooth cavity, preform, or restoration. Continuous fibers are distinct from short fibers (or "whiskers") in that the latter are discontinuously distributed in the matrix and each fiber is much shorter than the dimensions of the entire restoration. About 5% to 100% by weight of the fibers in the fiber material are continuous fibers. Preferably, at least about 25% by weight of the fibers in the fiber material are continuous fibers. Continuous fibers may comprise, for example, a minimum of 35%, 45%, or 60% by weight of the fiber material.

Examples of fibers which may be used include glass fibers, ceramic fibers, polymer fibers, metal fibers, and mixtures thereof. Transparent or translucent fibers with refractive indices matching those of dental resins are especially preferred when aesthetics are an important consideration. The fibers may be in aligned, uniform, uni-directional, mesh, tape, woven, thread, rope, random, and/or other useful forms. The fibers optionally are mixed with conventional fluoride-releasing or therapeutic fillers.

Dental resin monomers, such as those containing Bis-GMA and TEGDMA, optionally are mixed with the fibers. Preferably, the resin first is mixed with pre-hardened glass ionomer particles. The pre-hardened glass ionomer particles may be obtained, for example, by grinding a hardened glass ionomer or resin-modified glass ionomer into fine powders. The ground powders preferably are silanized (surface coated or surface treated), for example, by immersing in liquid 3-methacryloxypropyl-trimethoxysilane (MPTMS) and then dried. The filler level may range from about 5% to about 80%, preferably 20% to 40% by weight, to ensure adequate fluoride release while maintaining sufficient paste fluidity for coating onto the fiber bundles or meshes. As will be apparent to those skilled in the art, other known fillers also may be added into the resin for aesthetic and/or therapeutical purposes. The fiber level can range from about 5% to 90%, preferably from about 30% to 60% by weight. Unless otherwise indicated, all weight percentages recited herein are based on the total weight of the fiber material and the direct filling material, including any fillers which may be present.

Prior to direct filling the tooth cavity, the tooth cavity can be prepared in accordance with well-known techniques. Preferably, a liner is applied. The fiber material can then be placed into the prepared tooth cavity. The remainder of the space in the tooth cavity can then be filled with a conventional direct filling material, and the direct-filling material can be hardened, for example, by light, heat, pressure, chemical initiation, or combinations thereof.

Similarly, dental indirect restorations can be made. Fiber material can be placed into a mold. A composite resin filling material can be added to the mold. The composite resin filling material can then be hardened. The fiber material can be a hardened, continuous fiber composite preform; an unhardened, continuous fiber-resin paste; a partially-hardened, flexible, continuous fiber preform; or continuous fibers per se as previously defined. The filling material can be hardened by any suitable medium such as light, heat, pressure, chemical initiation, or combinations thereof. The hardened restoration can be bonded into a prepared tooth cavity or onto a prepared tooth.

Alternately, continuous fiber preform can be prepared by providing glass fibers, ceramic fibers, polymeric fibers, metal fibers, or mixtures thereof. A resin can be coated onto the fibers, and the resin can be hardened, e.g., in a mold, to form a composite fiber preform in which fibers extend continuously through at least 60% of the widest dimension. The resin may be hardened by any suitable medium such as light, heat, pressure, chemical initiation, or combinations thereof. During manufacture of the preforms, an oxygen-inhibiting layer preferably is preserved on the surface of the preform. One way to achieve this is to use oxygen-permeable molds during fabrication. The oxygen-inhibiting layer eliminates the need for further surface treatment to improve bonding to the surrounding composite in the restoration.

In an alternative embodiment, a preform can be prepared by coating a resin onto fibers. The resin can be hardened to form a composite fiber mass. The composite fiber mass can be cut and/or machined into a preform or preforms in which fibers extend continuously through at least 60% of the widest dimension.

Preforms can be molded or shaped into sizes and shapes suitable for direct insertion into tooth cavities, or alternately, into sizes and shapes suitable for use as endodontic posts, retention pins, provisional restorations, or indirect restorations. Preforms preferably have shapes and features for improving placement convenience. For example, a handle can be formed onto the preform by using a hybrid composite perpendicular to the preform that will fit into a carrying instrument or locking cotton plier. The handle may be shaped and contoured with the veneering composite once the total restoration is adequately cured.

Dental restoration kits according to the present invention include at least one continuous fiber preform, as described above, and a composite filling material. Preferably, the kit includes a plurality of continuous fiber preforms which differ from one another by shape and/or size. The kit also may also include one or more dummy preforms having substantially equal size and shape as the continuous fiber preform(s). The dummy preform enables a user to determine the size and shape of a preform needed for a particular tooth cavity. The kit preferably includes a tool for holding and placing both the fiber-reinforced preform and the filling material.

The restorations made in accordance with the invention possess 2 to 4 times higher strength than current composite resins, 6 to 20 times higher toughness than current composites, 2 to 3 times higher stiffness (modulus) than current composites, significantly less polymerization shrinkage, easy handling and replacement, enhanced aesthetics, and improved wear compatibility.

EXAMPLES

The following examples are provided for a more complete understanding of the invention. These examples are illustrative of preferred aspects of the invention and are not intended to limit the scope of the invention.

Example 1

This example illustrates the reinforcement of a large MOD (mesial occlusal-distal) restoration with pre-formed continuous fiber composites. A large MOD restoration has primarily tensile stresses at the internal aspect and compressive stresses at the occlusal. Fibers are oriented mesial-distal on the lower side of the insert, and in a random orientation or a bi-directional weave on the occlusal. Marginal ridge areas on the occlusal are under tensile stress so fibers can be oriented linearly mesial-distally towards the outer edge of the insert. Composites with the greatest compressive strength and highest wear resistance, but not necessarily the greatest flexural strength, such as a hybrid resin composite, are used as the occlusal veneer layer. The underlying fiber bundle provides toughness and flexural resistance while the overlying composite provides surface durability.

Example 2

This example illustrates preparing continuous fiber preforms for direct filling applications. A dental resin monomer is filled with pre-hardened glass ionomer powders to form a flowable paste. The paste is then coated onto a fiber bundle, and the bundle is hardened into a solid, composite rod which then is cut into sizes and shapes suitable for direct filling into tooth cavities. The coating is performed while the fiber bundle is lightly stirred to ensure infiltration of resin into the inter-fiber spaces to wet the fibers. The coated fiber bundle is then pulled through a hole or tube of an appropriate size to squeeze out excess resin and to minimize air bubbles, while being hardened by light. Chemically-initiated hardening or heat hardening is alternately performed.

While partially-hardened composite bundles are more flexible, more thoroughly hardened fiber composite bundles significantly reduce the polymerization shrinkage of the final restoration, especially when the hardened fiber composite preform takes a large portion of the tooth cavity. After the fiber composite preform is placed into the prepared tooth cavity, other direct-filling materials such as composite resin are used to fill the gaps and veneer the restoration.

Prior to being impregnated into the fibers, the resin can be unfilled or filled with desirable fillers, colorants, and powdered polyacid and fluorosilicate glass for fluoride release and adhesion to teeth. The filled resin paste then is coated onto the continuous fibers to make preforms. Various types and compositions of fibers may be used, including glass fibers, ion-releasing fluorosilicate glass fibers, bioactive fibers, ceramic fibers, metal fibers, and polymer fibers.

In addition to fiber bundles, other forms of fibers also may be used including fiber meshes, woven fiber tapes, sheets, ropes, and threads. In making the fiber composite preforms, pressure optionally is applied to squeeze out excess resin and air bubbles.

Example 3

This example illustrates a pultrusion technique to make continuous fiber-reinforced composite preforms The fibers are aligned and maintained in position as they are pulled through a bath of dental resin. Appropriate tensile stresses are applied to keep the fibers in position while the resin paste is impregnated and effectively wets the individual fibers. The coated fibers are then pulled to leave the resin bath and to go through rollers or holes to squeeze out excess resin and air bubbles, as well as to develop desirable dimensions and shapes, and then hardened. The hardened fiber composite is cut into preforms suitable for filling into tooth cavities.

Example 4

This example illustrates fabricating fiber composite preforms using a one-piece or two halves of a hollow tube. Transparent (e.g., glass or quartz) tubes (e.g., a square hole with an edge length of 1 mm, or a cylindrical hole with a diameter of 1 mm) are used for hardening by light. The continuous-fibers are loaded into the hollow tube. A dental resin is coated onto the fibers in the tube, preferably with pressure to wet the fibers and to squeeze out air bubbles. Appropriate tensile stresses are applied to keep the fibers in position in the transparent tube while the mixture is hardened by light. The tube is then broken to obtain the fiber composite rod. The fiber composite rod is cut into assorted sizes suitable for filing into tooth cavities (e.g., length ranging from 0.5 mm to 10 mm).

Example 5

This example illustrates forming preforms by cutting and/or machining. A block of continuous fiber-reinforced dental composite is hardened by light, chemical initiation, heat, and/or pressure. The block then is machined by conventional cutting, milling, grinding, and/or computer-assisted machining, into preforms of desired shapes and sizes suitable for direct insertion into tooth cavities.

Example 6

This example illustrates direct-filling a tooth cavity with free fibers that are not pre-impregnated with resin. Fiber bundles or meshes are cut into assorted, suitable sizes. A tooth cavity is prepared and the fibers are inserted into the prepared tooth cavity. A dental resin is impregnated into the fibers. The rest of the cavity is filled with direct-filling materials such as composite resin, and the entire restoration is hardened.

Example 7

This example illustrates a direct-filling method using glass ionomer cement. Fiber preforms are used to reinforce restorations with fluoride release. A tooth cavity is prepared, then partially filled with glass ionomer cement or other materials possessing desirable therapeutic functions. A layer of fibers or fiber composite preform is placed on top of the glass ionomer. Optionally, a liner or a flowable resin is used to fill the gaps and bond the fibers, which may be either hardened or unhardened. The rest of the cavity is then filled with a direct-filling material such as a composite resin, and the final restoration is hardened.

Alternatively, a tooth cavity is prepared, then filled with a layer of fibers or a fiber composite preform. Glass ionomer cements or other materials possessing desirable therapeutic functions are then filled on top of the fibers. These materials then are covered with another layer of fibers or fiber composite preform. The rest of the cavity is filled and veneered with a direct-filling material such as composite resin, and the final restoration is hardened.

The fiber composite alternately may be used as a strong core. A tooth cavity is prepared. A liner and/or a flowable resin optionally is used to fill a portion of the cavity. Then a fiber bundle or a fiber composite preform is inserted into the cavity. The rest of the cavity is filled with a direct-filling material such as a composite resin, and the final restoration is hardened.

Example 8

This example illustrates endodontic posts fabricated from rod-shaped, continuous-fiber preforms. The endodontic posts have high flexural strength, like current graphite rods, but are translucent, allowing light into the root and restoration This is aesthetically acceptable for all ceramic crowns on endodontically-treated anterior teeth or anterior teeth fractured at the root level. In addition, the endodontic posts can release fluoride by incorporating pre-hardened glass ionomer particles into the fiber composite preform.

Example 9

This example illustrates continuous-fiber reinforced retention pins. Small rod-like fiber composite preforms, approximately 3 mm in length and 0.5 mm in diameter, are used as reinforcement/retention pins in composite restorations. The pin may have both adhesive and mechanical features for retention. For example, pin holes may be drilled into dentin and enamel, and the pin cemented into the tooth with dentin/enamel adhesives. The restoration may be built up around the pin, thus increasing the retention and resistance of the final restoration. This is particularly useful for large class V fractures of anterior teeth and for teeth broken close to the gum line where retention is lacking for a restoration or buildup. Major advantages of this configuration include the aesthetics of the fiber composite pin more closely matching the composite and the ability to adhesively retain both the pin and the surrounding restorative material.

Example 10

This example illustrates continuous-fiber reinforced provisional restorations. Provisional restorations are made as shell-shaped preforms of individual teeth with fiber reinforcement incorporated just below the surface in a circumferential direction. These shells optionally are filled with acrylic, seated over a preparation, and cemented in conventional manners. The result is more durable provisional restoration with exceptional aesthetics for long-term provisions or low-cost permanent crowns. Radially fiber-reinforced crowns or restorations may also be fabricated in the laboratory.

Example 11

This example illustrates continuous-fiber reinforced core buildups. Core buildup preforms that are shaped as a hollow, tapered cylinder (i.e., thimble) with radial and linear fiber reinforcement are produced for use as an incorporated matrix for forming a core buildup. The hollow form optionally is filled with composite, seated over a post or a retentive pin, and allowed to polymerize in place. The core is then shaped with conventional diamonds to form the crown preparation. This speeds up the placement of the buildup on horizontally-fractured or severely broken-down teeth and provides a very rigid, low-flexure buildup.

Example 12

This example illustrates direct-filling a tooth cavity using a continuous fiber preform. A Class II cavity was prepared in each of ten extracted human third molars. A liner was applied in each cavity. A fiber composite preform was placed into the cavity. The resin in the pre-hardened fiber composite contained 20% by mass of pre-hardened glass ionomer powders. The rest of the tooth cavity was filled with a hybrid posterior composite resin (TPH™ Spectrum, Caulk/Dentsply, Milford, Del.) and hardened by light. The tooth was then immersed in water at 37° C. for 24 hours and then axially sectioned in the direction perpendicular to the fiber axes. The cross section was polished with 0.5 µm diamond paste and viewed in optical and scanning electron microscopes.

Figure 2:
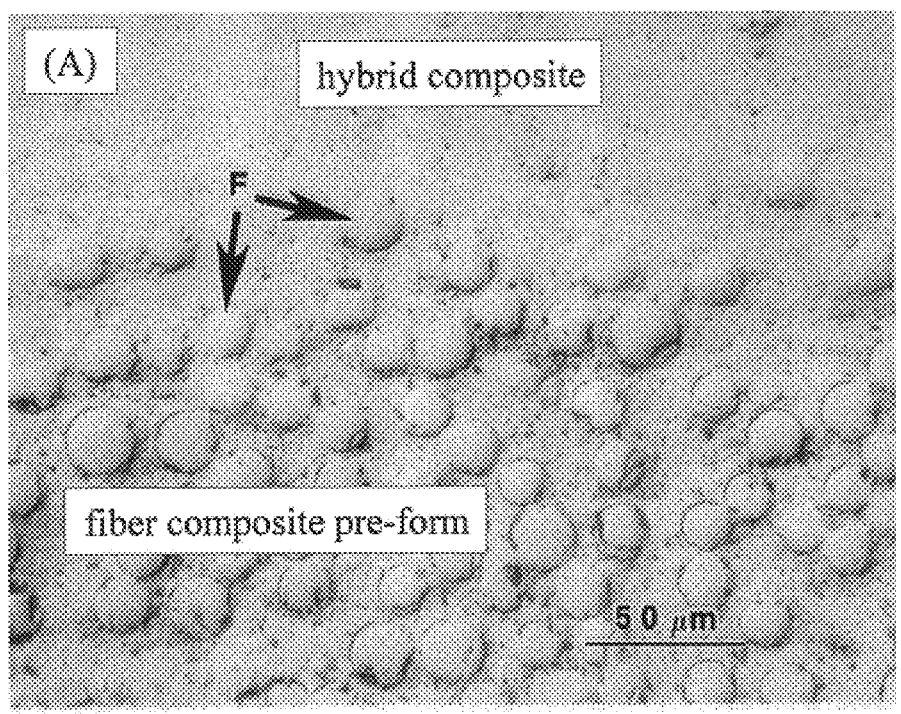
FIGS. 2A and 2B illustrates the interfacial regions between the continuous-fiber composite preform and the hybrid composite near the occlusal surface and the side enamel wall, respectively. In both cases, the fiber composite appears to be bonded to the hybrid composite.
Figure 2:
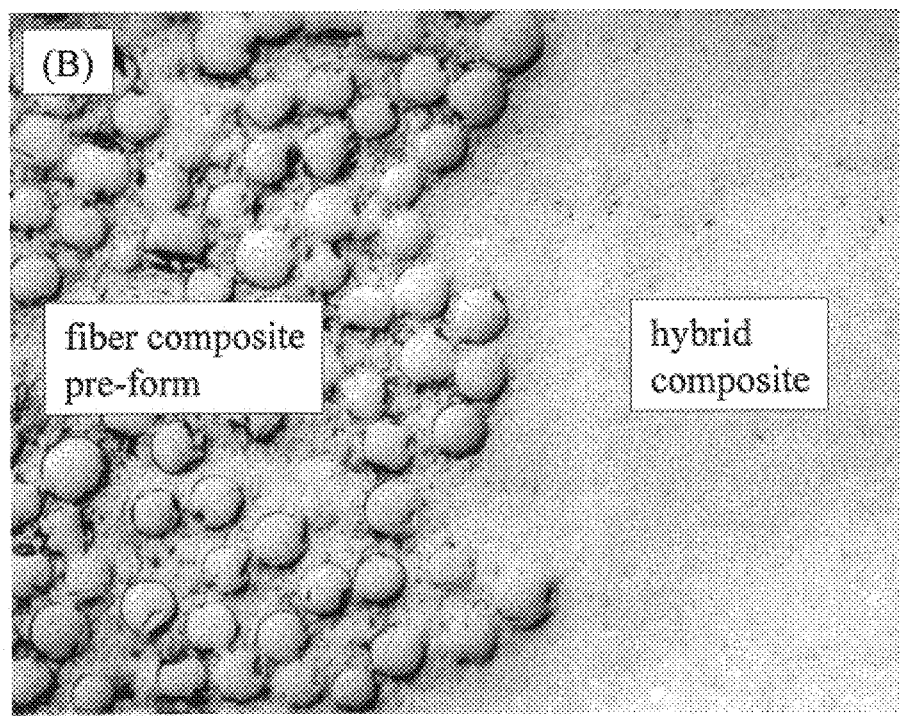
Figure 3:
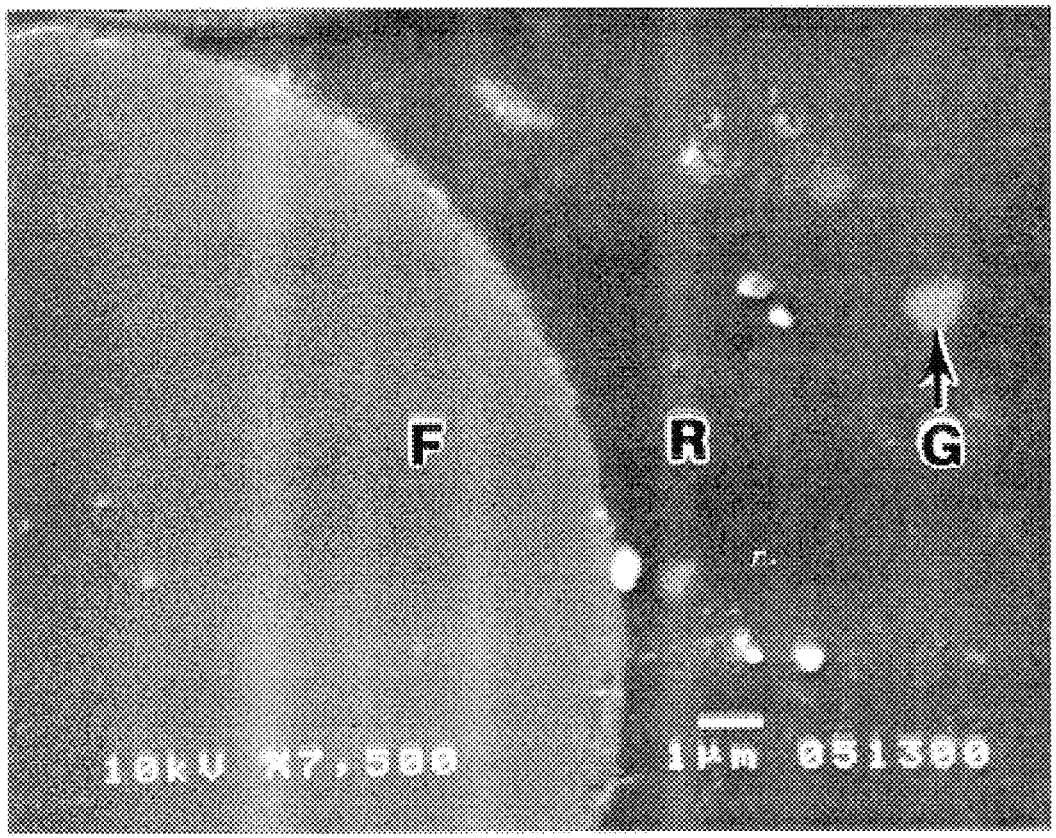
FIG. 3 is a scanning electron micrograph (SEM) showing the interfacial region between an individual fiber ("F") and the surrounding resin ("R"). Pre-hardened glass ionomer particles ("G") are also visible in the matrix. The fiber appears to be wetted by and bonded to the resin matrix.

FIG. 1 illustrates the fiber preform surrounded by a hybrid posterior composite beneath the occlusal surface. FIGS. 2A and 2B illustrates the interfacial regions between the continuous-fiber composite preform and the hybrid composite near the occlusal surface and the side enamel wall, respectively. In both cases, the fiber composite appears to be bonded to the hybrid composite. In FIG. 3, a scanning electron micrograph (SEM) shows the interfacial region between an individual fiber ("F") and the surrounding resin ("R"). Pre-hardened glass ionomer particles ("G") are also visible in the matrix. The fiber appears to be wetted by and bonded to the resin matrix.

Example 13

This example illustrates preparing pre-hardened, continuous fiber preforms. Flexural specimens were fabricated. A dental resin monomer, containing Bis-GMA and TEGDMA at a 1:1 mass ratio, was filled with 20 wt % of pre-hardened glass ionomer powder. Surface treatment was performed by mixing the fillers with 3-methacryloxypropyltrimethoxysilane (MPTMS) in cyclohexane containing n-propylamine as a catalyst, in a 90° C. water bath until dry. Continuous-fiber bundles were surface-treated by immersing in a glass beaker containing the MPTMS solution in a 90° C. water bath until dry. The treated fiber bundles were cut into a length of 24 mm, then inserted into a steel mold cavity of 2 mm×2 mm×25 mm. The resin monomer containing pre-hardened glass ionomer was then filled into the fibers in the mold cavity. The specimen was hardened by light for 1 minute at each side and then removed from the mold. The specimens were then incubated in distilled water at 37° C. for 24 hours prior to testing.

The specimens were fractured in a standard three-point flexural test (ASTM F417-78, 1984) to obtain the first-cracking strength (the applied stress required to produce the first crack in the matrix), the ultimate flexural strength (the maximum stress on the stress-strain curve), elastic modulus (or stiffness), and work-of-fracture (energy required to fracture the specimen; an indication of toughness), summarized in Table 1 below.

TABLE 1

Continuous-fiber reinforced dental composite resin containing 20 wt % pre-cured glass ionomer powders

| Mechanical properties | First cracking strength MPa ± sd (n = 6) | Ultimate strength MPa ± sd (n = 6) | Elastic modulus GPa MPa ± sd (n = 6) | Work-of-fracture kJ/m$^2$ ± sd (n = 6) |
|---|---|---|---|---|
| Fiber composite | 458 ± 41 | 458 ± 41 | 10.8 ± 0.8 | 19.7 ± 4.1 |

A veneer layer of a microfill composite (Silux™, 3M Co., St. Paul, Minn.) was placed on top of the fiber layer and the specimen was then hardened by light for 1 minute on each side. Two thickness values of the microfill veneer/fiber composite were tested: 0.2 mm/1.8 mm, and 0.7 mm/1.3 mm. The specimens were fractured in three-point bending with the microfill layer in tension to simulate the worst case scenario. The microfill specimens without the fiber layer reinforcement were fabricated in the same mold and tested using the same procedures for comparison. The results are listed in Table 2.

The microfill/fiber composite had significantly larger strength, modulus and work-of-fracture values than those of the control without fiber reinforcement (family confidence coefficient=0.95, Tukey's Multiple Comparison Test), as indicated by different superscripts in each column of Table 2.

TABLE 2

Fiber composite containing glass ionomer powders veneered with a microfill composite resin tested with the microfill layer in tension*

| Composite | First Cracking strength MPa ± sd (n = 6) | Ultimate Strength MPa ± sd (n = 6) | Modulus GPa ± sd (n = 6) | Work-of-fracture kJ/m$^2$ ± sd (n = 6) |
|---|---|---|---|---|
| Microfill (Silux ™) composite control | 49 ± 5$^c$ | 49 ± 5$^c$ | 2.9 ± 0.3$^B$ | 0.5 ± 0.1$^b$ |
| 1.3 mm thick fiber composite reinforcement | 118 ± 19$^B$ | 211 ± 44$^b$ | 7.0 ± 1.2$^A$ | 11.9 ± 4.0$^a$ |
| 1.8 mm thick fiber composite reinforcement | 184 ± 9$^A$ | 335 ± 40$^a$ | 9.3 ± 1.5$^A$ | 12.8 ± 2.6$^a$ |

*Within each column, values with the same superscripts are not statistically different (Tukey's multiple comparison test; family confidence coefficient = 0.95).

Example 14

This example illustrates preparing a hardened continuous fiber preform. A posterior hybrid composite resin (TPH™ Spectrum, Caulk/Dentsply, Milford, Del.) was used to veneer the fiber composite. The fibers were placed into the mold of 2 mm×2 mm×25 mm and mixed with a monomer containing 20% by mass of pre-hardened glass ionomer powders. Then a layer of posterior composite was placed on top of the fiber layer and the specimen was hardened by light for 1 minute on each side. Two thickness values of the posterior veneer/fiber composite were tested: 0.2 mm/1.8 mm, and 0.7 mm/1.3 mm. The specimens were fractured in three-point bending with the posterior composite layer in tension to simulate the worst case scenario. The posterior composite specimens without a fiber layer were fabricated in the same mold and tested using the same procedures for comparison. The results are listed in Table 3.

The posterior composite veneered continuous-fiber composite had significantly larger strength, modulus, and work-of-fracture values than those of the posterior composite without fiber reinforcement (family confidence coefficient=0.95; Tukey's Multiple Comparison Test), as indicated by different superscripts in each column in Table 3.

TABLE 3

Fiber composite containing glass ionomer powders veneered with a posterior composite resin tested with the posterior composite layer in tension*

| Composite | First cracking strength MPa ± sd (n = 6) | Ultimate strength MPa ± sd (n = 6) | Modulus GPa ± sd (n = 6) | Work-of-fracture kJ/m$^2$ ± sd (n = 6) |
|---|---|---|---|---|
| Posterior composite control (TPH ™) | 120 ± 16$^B$ | 120 ± 16$^b$ | 4.9 ± 0.8$^B$ | 2.4 ± 0.8$^c$ |
| 1.3 mm thick fiber composite reinforcement | 222 ± 11$^A$ | 330 ± 40$^a$ | 11.5 ± 0.7$^A$ | 14.1 ± 2.6$^b$ |
| 1.8 mm thick fiber composite reinforcement | 220 ± 18$^A$ | 295 ± 24$^a$ | 12.3 ± 0.6$^A$ | 17.5 ± 1.6$^a$ |

*Within each column, values with the same superscripts are not significantly different (Tukey's multiple comparison test; family confidence coefficient = 0.95).

Example 15

This example illustrates a hardened continuous fiber preform in which only a thin layer of the fiber composite of Example 14 was used. The specimen mold cavity of 2 mm×2 mm×25 was filled with a posterior composite of approximately 0.2 mm in thickness, then a fiber layer which was mixed with a resin monomer containing 20% by mass of pre-hardened glass ionomer powders was placed. Two thickness values of posterior composite/fiber composite/posterior composite were tested: 0.2 mm/0.2 mm/1.6 mm, and 0.2 mm/0.7 mm/1.1 mm. The results are listed in Table 4.

TABLE 4

Posterior composite resin reinforced with a thin layer of fiber composite containing glass ionomer powder tested with posterior composite in tension*

| Composite | First cracking strength MPa ± sd (n = 6) | Ultimate strength MPa ± sd (n = 6) | Modulus GPa ± sd (n = 6) | Work-of-fracture kJ/m$^2$ ± sd (n = 6) |
|---|---|---|---|---|
| Posterior (TPH ™) composite control | 120 ± 16$^B$ | 120 ± 16$^b$ | 4.9 ± 0.8$^C$ | 2.4 ± 0.8$^b$ |
| 0.2 mm thick fiber composite reinforcement | 181 ± 32$^A$ | 438 ± 58$^a$ | 9.5 ± 0.5$^B$ | 22.8 ± 4.0$^a$ |
| 0.7 mm thick fiber composite reinforcement | 231 ± 38$^A$ | 442 ± 43$^a$ | 11.7 ± 0.6$^A$ | 24.4 ± 5.5$^a$ |

*Within each column, values with the same superscripts are not significantly different (Tukey's multiple comparison test; family confidence coefficient = 0.95).

Example 16

This example illustrates molding a continuous fiber preform. A thin layer of fiber composite was placed on the tensile side. The specimen mold cavity (2 mm×2 mm×25 mm) was filled with a fiber layer mixed with a resin monomer containing 20% by mass of pre-hardened glass ionomer powders and cured. The rest of the mold cavity was then filled with a posterior composite and cured. Two thickness values of the fiber composite/posterior composite were tested: 0.2 mm/1.8 mm, and 0.4 mm/1.6 mm. The specimens were fractured in three-point bending with the fiber composite layer in tension. The results are listed in Table 5.

TABLE 5

Posterior composite resin reinforced with a thin layer of fiber composite containing glass ionomers, tested with the fiber layer in tension*

| Composite | First cracking strength MPa ± sd (n = 6) | Ultimate Strength MPa ± sd (n = 6) | Modulus GPa ± sd (n = 6) | Work-of-fracture kJ/m$^2$ ± sd (n = 6) |
|---|---|---|---|---|
| Posterior composite control (TPH ™) | 120 ± 16$^B$ | 120 ± 16$^b$ | 4.9 ± 0.8$^B$ | 2.4 ± 0.8$^b$ |
| 0.2 mm thick fiber composite reinforcement | 396 ± 11$^A$ | 396 ± 11$^a$ | 10.0 ± 0.5$^A$ | 15.5 ± 4.3$^a$ |
| 0.4 mm thick fiber composite reinforcement | 359 ± 44$^A$ | 359 ± 44$^a$ | 9.8 ± 0.6$^A$ | 17.7 ± 4.9$^a$ |

*Within each column, values with the same superscripts are not significantly different (Tukey's multiple comparison test; family confidence coefficient = 0.95).

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

What is claimed is:

1. A method for preparing a continuous fiber-reinforced restoration for direct filling a tooth cavity in a tooth having an occlusal surface, the method comprising:
   inserting into a prepared tooth cavity a fiber material selected from the group consisting of a hardened fiber composite preform, fibers, an unhardened fiber-resin paste, and a partially-hardened flexible fiber composite preform; wherein fibers in the fiber material extend continuously across at least 60% of the widest dimension of the tooth cavity, and wherein the fibers are oriented in a direction generally parallel to the occlusal surface of the tooth;
   filling the tooth cavity with a direct-filling material; and
   hardening the direct-filling material to form the continuous fiber-reinforced restoration.

2. The method of claim 1 wherein the fiber material consists of fibers and the direct-filling material is a resin monomer which forms a paste inside the tooth cavity.

3. The method of claim 2 wherein the direct-filling material further comprises pre-hardened glass ionomer particles.

4. The method of claim 2 wherein the fiber material comprises from about 5 to 90% of the combined weight of the direct filling material and fiber material.

5. The method of claim 2 wherein the fiber material comprises from about 30 to 60% of the combined weight of the direct filling material and fiber material.

6. The method of claim 1 wherein the fiber material consists of fibers and said fibers are coated with a dental liquid resin.

7. The method of claim 1 wherein the fiber material is a hardened fiber composite preform or a partially-hardened flexible fiber composite preform.

8. The method of claim 7 wherein the preform was fabricated in a mold.

9. The method of claim 7 wherein the preform was cut and machined to a size and shape suitable for insertion into the tooth cavity.

10. The method of claim 1 wherein the direct-filling material is selected from the group consisting of composite resin, glass ionomer cement, and resin-glass ionomer cement.

11. The method of claim 1 wherein the fiber material further comprises a fluoride-releasing filler.

12. The method of claim 1 wherein the fibers in said fiber material are selected from the group consisting of glass fibers, ceramic fibers, polymeric fibers, metal fibers, and mixtures thereof.

13. The method of claim 1 wherein at least about 25% of the fibers in the fiber material extend continuously through at least 60% of the widest dimension of the tooth cavity.

14. The method of claim 1 wherein at least about 35% of the fibers in the fiber material extend continuously through at least 60% of the widest dimension of the tooth cavity.

15. The method of claim 1 wherein at least about 45% of the fibers in the fiber material extend continuously through at least 60% of the widest dimension of the tooth cavity.

16. The method of claim 1 wherein at least about 60% of the fibers in the fiber material extend continuously through at least 60% of the widest dimension of the tooth cavity.

17. The method of claim 1 wherein at least about 25% of the fibers in the fiber material extend continuously through at least 65% of the widest dimension of the tooth cavity.

18. The method of claim 1 wherein at least about 25% of the fibers in the fiber material extend continuously through at least 70% of the widest dimension of the tooth cavity.

19. The method of claim 1 wherein at least about 25% of the fibers in the fiber material extend continuously through at least 75% of the widest dimension of the tooth cavity.

20. The method of claim 1 wherein at least about 25% of the fibers in the fiber material extend continuously through at least 80% of the widest dimension of the tooth cavity.

21. A method for preparing a continuous fiber-reinforced restoration for direct filling a tooth cavity in a tooth having an occlusal surface, the method comprising:

inserting into a prepared tooth cavity a fiber material consisting of polymeric fibers coated with and contained within a dental liquid resin;

filling the tooth cavity with a direct-filling material comprising a composite resin and pre-hardened glass ionomer particles, wherein the fiber material comprises from about 30 to 60% of the combined weight of the direct filling material and fiber material; and hardening the direct-filling material to form the continuous fiber-reinforced restoration;

wherein at least about 60% of the fibers extend continuously through at least 80% of the widest dimension of the tooth cavity, and wherein the fibers are oriented in a direction generally parallel to the occlusal surface of the tooth.

22. A method for preparing a continuous fiber-reinforced restoration for direct filling a tooth cavity in a tooth having an occlusal surface, the method comprising:

inserting into a prepared tooth cavity a fiber material consisting of a hardened composite polymeric-fiber preform;

filling the tooth cavity with a direct-filling material comprising a composite resin and pre-hardened glass ionomer particles; and hardening the direct-filling material to form the continuous fiber-reinforced restoration;

wherein at least about 60% of the fibers extend continuously through at least 80% of the widest dimension of the tooth cavity, and wherein the fibers are oriented in a direction generally parallel to the occlusal surface of the tooth.

23. A method for preparing a continuous fiber-reinforced dental indirect restoration for restoration of a portion of a tooth on the tooth crown, the method comprising:

placing a fiber material into a mold having a longitudinal axis, wherein the fiber material is selected from the group consisting of a hardened fiber composite preform, fibers, an unhardened fiber-resin paste, and a partially-hardened flexible fiber composite preform; wherein fibers in the fiber material extend continuously across at least 60% of the widest dimension of the mold;

adding a composite resin filling material to the mold;

hardening the composite resin filling material to form the continuous fiber-reinforced dental indirect restoration; and restoring a portion of the tooth crown by bonding the restoration into a prepared a tooth cavity in a tooth having an occlusal surface or onto a prepared tooth having an occlusal surface, wherein the fibers are oriented in a direction generally parallel to the occlusal surface of the tooth.

24. A method for preparing a continuous fiber-reinforced dental indirect restoration for restoration of a portion of a tooth on the tooth crown, the method comprising:

placing a fiber material into a mold having a longitudinal axis, wherein the fiber material consists of ceramic fibers;

adding a composite resin filling material to the mold;

hardening the composite resin filling material to form the continuous fiber-reinforced dental indirect restoration; wherein at least 60% of the fibers in the fiber material extend continuously through at least 80% of said restoration of the tooth crown; and restoring a portion of the tooth crown by bonding the restoration into a prepared a tooth cavity in a tooth having an occlusal surface or onto a prepared tooth having an occlusal surface, wherein the fibers are oriented in a direction generally parallel to the occlusal surface of the tooth.

* * * * *

UNITED STATES PATENT AND TRADEMARK OFFICE
CERTIFICATE OF CORRECTION

PATENT NO.    : 6,334,775 B2
DATED         : January 1, 2002
INVENTOR(S)   : Huakun Xu, Frederick C. Eichmiller and Gary E. Schumacher It is certified that error appears in the above-identified patent and that said Letters Patent is hereby corrected as shown below:

Column 1,
Line 5, please add the following language as paragraph one:

-- This invention was supported in part by research grant number DE12476 to the American Dental Association Health Foundation from the National Institute of Dental Research. The Government has certain rights in this invention. --

Signed and Sealed this

Fourth Day of March, 2003

JAMES E. ROGAN
*Director of the United States Patent and Trademark Office*